United States Patent [19]

Nyberg

[11] Patent Number: 4,724,061
[45] Date of Patent: Feb. 9, 1988

[54] AUTOMOTIVE, INTERNAL REFERENCE, SOLID ELECTROLYTE, LEAN OXYGEN SENSOR

[75] Inventor: Glen A. Nyberg, Warren, Mich.

[73] Assignee: General Motors Corporation, Detroit, Mich.

[21] Appl. No.: 898,623

[22] Filed: Aug. 21, 1986

[51] Int. Cl.⁴ .............................................. G01N 27/46
[52] U.S. Cl. .................................... 204/412; 204/426; 204/427
[58] Field of Search ............... 204/421, 424, 425, 426, 204/427, 428, 429, 412

[56] References Cited

U.S. PATENT DOCUMENTS

| | | | |
|---|---|---|---|
| 4,158,166 | 6/1979 | Isenberg | 324/29 |
| 4,272,350 | 6/1981 | Croset et al. | 204/426 |
| 4,296,148 | 10/1981 | Friese | 204/426 |
| 4,354,912 | 10/1982 | Friese | 204/426 |
| 4,462,890 | 7/1984 | Touda et al. | 204/425 |
| 4,487,680 | 12/1984 | Logothetis et al. | 204/426 |
| 4,571,285 | 2/1986 | Nakazawa et al. | 204/425 |

FOREIGN PATENT DOCUMENTS 0104636  4/1984  European Pat. Off. .
2087569  5/1982  United Kingdom ................ 204/421

OTHER PUBLICATIONS

Measurements of Chemical Diffusion Coefficients in Non-Stoichiometric Oxides Using Solid State Electrochemical Technique by B. C. H. Steele and C. C. Riccardi, pp. 123-135.

Primary Examiner—John F. Niebling
Assistant Examiner—Ben C. Hsing
Attorney, Agent, or Firm—Robert J. Wallace

[57] ABSTRACT

Rapid response, highly precise determinations of oxygen partial pressures in internal combustion engines operating with lean air/fuel mixtures are accomplished by using a thin film internal reference, solid electrolyte electrochemical type oxygen sensor comprising laterally disposed galvanic sense and pump cells on a single planar substrate, and an internal reference gas chamber provided by a cap. A cerium dioxide, thin film electrode on the galvanic pump cell provides an oxygen reservoir for the internal reference gas chamber.

4 Claims, 2 Drawing Figures

AUTOMOTIVE, INTERNAL REFERENCE, SOLID ELECTROLYTE, LEAN OXYGEN SENSOR

The present invention generally relates to automotive exhaust gas oxygen sensors of the solid electrolyte, electrochemical type. More specifically, this invention relates to thin film, rapid response, high precision, internal reference, solid electrolyte oxygen sensors for lean internal combustion conditions.

BACKGROUND OF THE INVENTION

Gas sensors are employed in a variety of applications requiring qualitative and quantitative gaseous determinations. In the automotive industry, it is well known that the oxygen concentration in the automobile exhaust has a direct relationship to the engine air-to-fuel ratio. Oxygen gas sensors are employed within the automobile internal combustion control system to provide accurate exhaust gas oxygen concentration measurements for determination of optimum combustion conditions, maximization of efficient fuel usage, and management of exhaust emissions.

Typically, the electrochemical type of oxygen sensor employed in automotive applications utilizes a thimble-shaped electrochemical galvanic cell to determine, or sense, the relative amounts of oxygen present in the exhaust stream, as disclosed in U.S. Pat. No. 3,844,920 to Burgett et al. This type of oxygen sensor comprises an ionically conductive solid electrolyte material, typically yttria stabilized zirconia, a porous electrode coating on the exterior exposed to the exhaust or measuring gas and a porous electrode coating on the interior exposed to a known concentration of reference gas. The gas concentration gradient across the solid electrolyte produces a galvanic potential which is related to the differential of the partial pressures of the gas at the two electrodes by the Nernst equation: $E = AT \ln[P_1/P_2]$, where E is the galvanic voltage, T is the absolute temperature of the gas, $P_1/P_2$ is the ratio of the partial pressures of the reference gas at the two electrodes, and $A = R/4F$, where R is the universal gas constant and F is the Faraday constant.

Currently, these oxygen sensors are employed in the exhaust gas system of an internal combustion engine to determine qualitatively whether the engine is operating at either of two conditions: (1) a fuel rich or (2) a fuel lean condition, as compared to stoichiometry. After equilibration, the exhaust gases from these two operating conditions have two widely different oxygen partial pressures. This information is provided to an air-to-fuel ratio control system, so that it can provide an average stoichiometric air-to-fuel ratio between the two conditions. However, due to increasing demands for improved fuel utilization and emissions control, it is desirable to operate internal combustion engines exclusively within lean combustion conditions, i.e., air-to-fuel ratio between 15:1 and 25:1, where changes in the after-combustion oxygen partial pressures are only gradual and slight. The current oxygen sensor is not sensitive enough for this latter type of environment.

To be an effective component of the internal combustion control system operating exclusively within lean combustion conditions, the oxygen sensor must be extremely sensitive and capable of rapid, precise, absolute oxygen concentration measurements. It is desirable that the sensor must have a response time of less than 0.1 second at a minimum temperature of 300° C. and a maximum oxygen concentration at the sensing electrode of about eight percent. To prevent false sensor readings, the sensor should be hermetically sealed, and must also be free from any current leakage caused by electronic conduction in the solid electrolyte body. The sensor must be structurally sound to withstand the considerable vibration and wide temperatures ranges, −40° C. to 800° C., that it may be exposed to. Most importantly, the sensor should be amenable to mass production.

Internal reference oxygen sensors have been devised for lean engine operation and typically comprise two solid electrolyte galvanic cells: the first galvanic cell senses the gas to be measured, while the second galvanic cell generates an accurately known internal gas reference. The accurately known internal gas reference is generated by electrochemically pumping oxygen gas into and out of a hermetically sealed, fixed volume chamber by means of the second galvanic cell. An external power source provides a potential across the solid electrolyte body of the second galvanic cell. Electrons supplied at one electrode ionize gas molecules at the interface between that negatively biased electrode and the solid electrolyte. The gas ions are then transported through the solid electrolyte by ionic conduction. At the other electrode, the gas ions lose electrons and recombine into gas molecules. By reversing the polarity of the external circuit, oxygen gas can be transported in the other direction and subsequently pumped out of the hermetically sealed, fixed volume chamber. The partial pressure (i.e., concentration) of oxygen gas in a gas mixture can be measured by simultaneously sensing the oxygen partial pressure differential between the internal reference chamber and the gas mixture with the first galvanic cell.

In the past, internal reference, solid electrolyte gas sensors have generally comprised two discrete galvanic cells bonded within a cylinder or bonded together to form a hermetically sealed, fixed volume chamber. These sensors are difficult and expensive to assemble due to the inherent problems associated with hermetic sealing, and therefore are not suitable for a mass production device. An improvement is disclosed in U.S. Ser. No. 882,689 filed July 7, 1986, now U.S. Pat. No. 4,668,374 by J. K. Bhagat and D. S. Howarth entitled, "Gas Sensor and Method of Fabricating Same" and assigned to the assignee of this invention. The improvement involves laterally positioning both the pump and sense cell components on a single substrate, resulting in a simpler, more efficient, and easier to produce device. In this improvement, pump and sense cells can be disposed in a cavity in the substrate and encased by a hermetically bonded cover plate. Apertures in the substrate expose appropriate electrodes of the pump and sense cells for operation.

Internal reference, solid electrolyte oxygen sensors may be operated in various modes to determine gas concentration measurements. One method is to pump oxygen into the internal reference gas chamber with the pump cell until the pressure therein produces a voltage output at the sense cell that equals zero or a threshold value. The period of time required to pump that amount (i.e., pressure) of oxygen into the reference gas chamber is related to the oxygen partial pressure in the exhaust gas. An alternative method is to maintain a constant oxygen pressure in the internal reference gas chamber and determine exhaust oxygen concentration from the voltage output measurements at the sense cell.

If one elects to cycle oxygen out of and back into the reference chamber each time one chooses to measure oxygen partial pressure in a gas mixture, sensor response time will be proportional to the volume of the internal gas reference chamber, i.e., the number of gas molecules needed to be pumped into and out of the chamber in order to reach a reference pressure. It is desirable to keep the chamber volume to a minimum in order to maximize the quickness of sensor response. Currently, as in the previously mentioned U.S. Ser. No. 882,689, the thickness of the material employed to bond the two substrates comprising the pump and sense cell components limits the minimum chamber volume attainable. Therefore, a solution is to employ a single substrate as the support for both the pump and sense cell components. My invention comprehends a single substrate and uses conventional thin film deposition techniques to produce a chamber of lesser volume.

Sensor response time is also related to the thickness of the solid electrolyte and its ionic resistance. A thin electrolyte film produces a short response time. However, in the aforementioned type of constructions, the electrolyte film must be thick enough to be structurally sound. One typical prior internal reference solid electrolyte oxygen sensor comprises two discrete solid electrolyte concentration cells hermetically sealed together. Each cell is a solid electrolyte disk that is electroded on its opposite faces. Because each solid electrolyte disk provides the entire structural support for the concentration cell, the solid electrolyte disk is accordingly rather thick, and the sensor rather slow in responding. In my invention, we use an alumina substrate to provide support for thin film solid electrolyte layers having thin film porous electrodes.

In the previously filed U.S. Ser. No. 882,689, an internal reference, solid electrolyte oxygen sensor is disclosed comprising thinner solid electrolyte layers than prior internal reference, solid electrolyte sensors. The electrolyte layers are disposed on a substrate in a chamber formed between the substrate and cover member. However, in order to provide access to the exhaust gas at one of the porous electrodes comprised within sense cell, the supporting substrate under the sense cell components must be removed. Subsequently, the solid electrolyte film becomes the structurally supporting member for the porous platinum electrodes. Thus, for strength purposes, a considerable thickness of solid electrolyte material is needed, over that which would be required for electrical performance purposes alone. It is desirable to provide some alternative form of structual support to all components of the oxygen sensor, including the electrolyte layer, so that thicknesses of the component layers can be minimized and sensor response time reduced without any detrimental loss to structural integrity.

SUMMARY OF THE INVENTION

It is an object of my invention to provide a miniature oxygen sensor capable of precise, reliable, rapid oxygen concentation measurements for internal combustion engines operating in lean air-to-fuel environments. It is a further object of my invention to provide an internal reference oxygen chamber and an electrode contained within the pump cell comprised of a cerium dioxide layer, such that the cerium dioxide layer provides a reservoir for the volume of oxygen pumped into and out of the internal reference gas chamber. It is still a further object of my invention that such oxygen sensor should be amenable to mass production.

In accordance with a preferred embodiment of my invention, these and other objects and advantages are accomplished as follows.

This invention comprehends a thin film, rapid response, highly precise, internal reference, solid electrolyte oxygen sensor. Galvanic sense and pump cells are laterally disposed and totally supported on top of a non-ionically and non-electrically conductive substrate, preferably alumina. The galvanic sense cell comprises an yttria stabilized zirconia solid electrolyte film and two overlaying porous platinum electrodes that are mutually laterally disposed on the electrolyte layer. In operation, the first electrode contacts the external measuring gas and the second electrode contacts the internal reference gas. The galvanic pump cell comprises an yttria stabilized zirconia solid electolyte film and an overlaying porous platinum electrode that is exposed to the internal reference gas during sensor operation. The second electrode of the pump cell is provided by a thin film of cerium dioxide, also commonly referred to as ceria or $CeO_2$, under the electrolyte film. A hermetically sealed, impermeable cap provides the internal reference gas chamber of minimal volume by covering the second electrode of the sense cell and the first electrode of the pump cell, leaving both electrodes exposed within the chamber for contact with the internal reference gas.

My invention contemplates a miniature chamber volume of about 2500 to 9000 cubic microns. It also contemplates that as the chamber volume becomes minimal as in my invention, sensor response time is further improved if the oxygen molecules are reversibly pumped into the walls of the second electrode of the pump cell instead of through the entire electrode as current internal reference solid electrolyte oxygen sensors do. The second electrode in the pump cell must therefore be of a material that is not only electrically conductive but also must be capable of reacting reversibly with oxygen molecules and exhibit good stability at high levels of nonstoichiometry. In my invention, a cerium dioxide thin film comprises the second electrode of the pump cell. Cerium dioxide reversibly reacts with oxygen gas and has good stability at high levels of nonstoichiometry. The ceria electrode is employed as an oxygen reservoir, allowing the oxygen to be pumped into its walls rather than through it, and subsequently resulting in an improved sensor response time and more efficient oxygen sensor.

Other objects and advantages of my invention will be better appreciated from the following detailed description.

DETAILED DESCRIPTIION OF THE INVENTION

Figure 1:
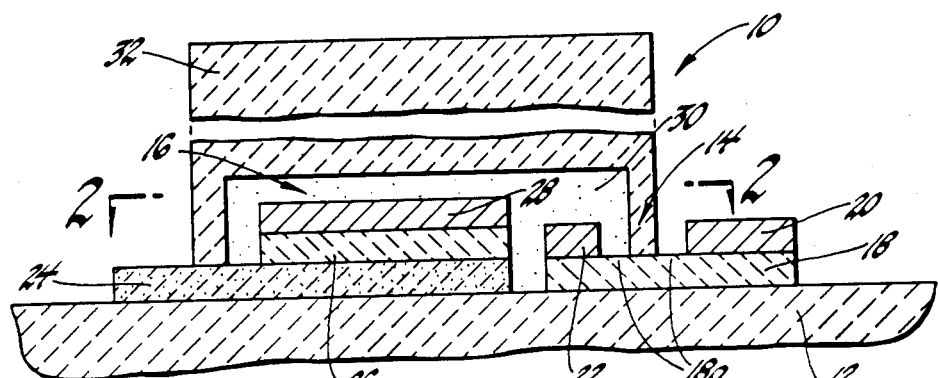
FIG. 1 is a cross-sectional view of a thin film, internal rererence, solid electrolyte oxygen sensing device in accordance with a preferred embodiment of this invention and illustrates the galvanic sense and pump cells, internal reference gas chamber, capping layer, and substrate.

A highly polished alumina substrate 12, 2.5 centimeters in diameter and 1.0 centimeter thick, is the preferred material for the supporting member in the preferred embodiment of my invention. Other non-ionically conductive materials may also be employed. Using conventional thin film deposition techniques, solid electrolyte galvanic sense and pump cells 14 and 16 respectively, and hereinafter referred to as the sense cell and pump cell respectively, are laterally disposed on about a 200 micron square area on the planar surface of the alumina substrate.

The sense cell 14 comprises a film 18 of conventional solid electrolyte material, preferably zirconia partially or fully stabilized in its cubic form by the inclusion of about 4-8 mole percent yttria and two laterally deposited porous platinum electrodes 20 and 22. The yttria stabilized zirconia film 18 is deposited to a thickness of about 0.1 to about 1.0 microns. This thickness has no significant strength and is not appreciably self supporting. However, in the construction shown the yttria stabilized zirconia, solid electrolyte film 18 does not need to be. Means (not shown) are provided by which the first porous platinum electrode 20 contacts the gaseous mixture whose oxygen content is to be measured, i.e., the exhaust gases. The second porous platinum electrode 22 is provided for contact with the internal reference gas, the pumped oxygen gas. Both porous platinum electrodes are sputtered to a thickness of about 0.1 to about 1.0 microns. It is preferred that the thicknesses of the yttria stabilized zirconia, solid electrolyte film and porous platinum electrodes not exceed about 0.3 microns. This amount of material appears optimal in order to ensure sufficient coverage without sacrificing sensor response time. However, no significant detrimental effects have been observed when the films are deposited to thicknesses of about 1.0 micron.

Figure 2:
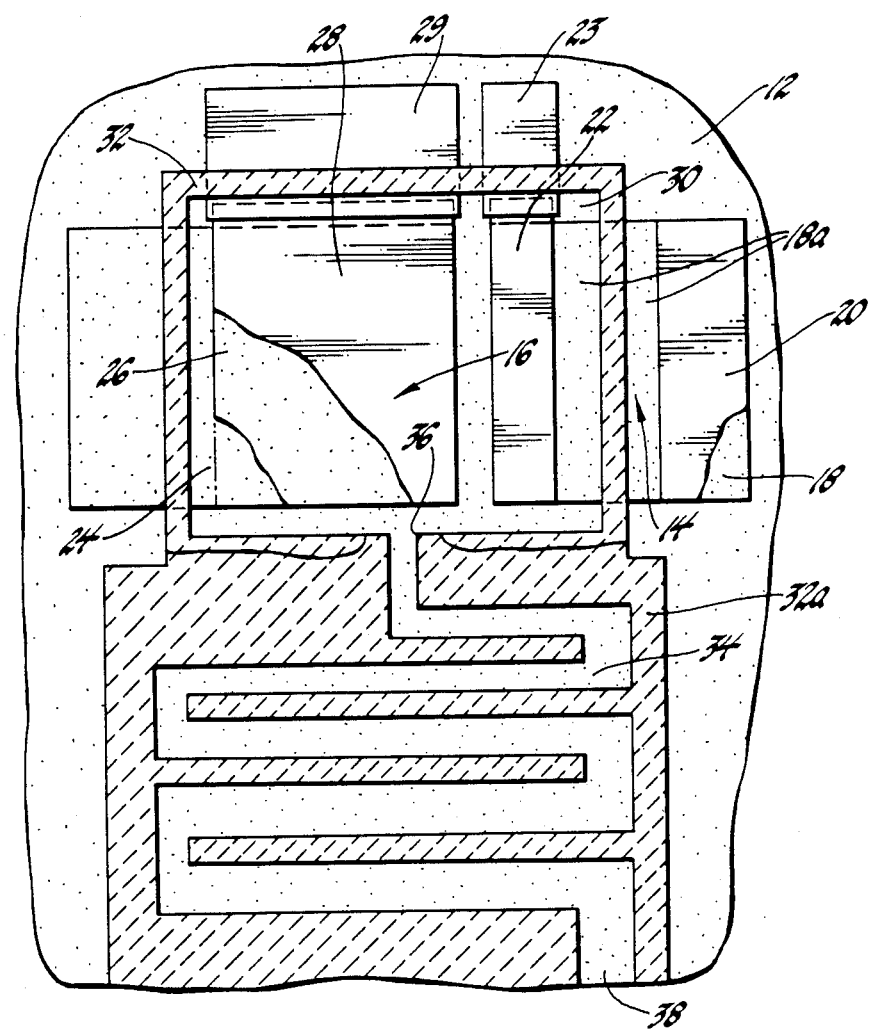
FIG. 2 is a plan view along the line 2—2 of the oxygen sensing device shown in FIG. 1

The sense cell 14 comprises a rectangular shaped solid zirconia electrolyte film 18 as depicted in FIG. 2, about 80 microns wide and 50 microns long, on top of the highly polished alumina substrate 12. The first platinum electrode film 20 is rectangular, about 30 microns wide by about 50 microns long, and is positioned on the one end of the solid zirconia electrolyte film which will subsequently contact the exterior gas to be measured. The second platinum electrode film 22 is also rectangular, about 20 microns wide by about 50 microns long, and is positioned on the opposite end of the solid zirconia electrolyte film from the first electrode. A rectangular film 23, about 25 microns wide by about 100 microns long, of non-porous electrically conductive material, such as non-porous platinum, overlaps a portion of the second porous platinum electrode and extends approximately 90 microns beyond the zirconia film onto the highly polished alumina substrate, as shown in FIG. 2. The thickness of this electrically conductive film is about 0.1 to about 1.0 micron, with the optimal thickness again being about 0.3 micron. This non-porous electrically conductive film 23 provides the electrical contact needed for the internal combustion control system. A non-porous material is needed so that oxygen gas from the internal reference gas chamber cannot leak through the second porous platinum electrode. A band 18a of exposed and uncovered zirconia film, about 30 microns wide and about 50 microns long, is provided between the two electrodes.

The pump cell 16 is positioned alongside the sense cell 14 on top of the alumina substrate 12 and separated from the sense cell by a gap about 20 microns wide. The second electrode 24 of the pump cell 16 is deposited first on top of the alumina substrate 12 and patterned to form a rectangle, about 100 microns wide and about 50 microns long. The solid electrolyte zirconia film 26 is deposited on top of the second electrode 24 and positioned at the end of the second electrode nearest to the sense cell. The zirconia film 26 is patterned to form approximately a 50 micron square. The first electrode 28 is then deposited on top of the zirconia film 26 and patterned to form approximately a 50 micron square. A rectangular shaped, non-porous electrically conductive thin film 29, such as non-porous platinum, about 55 microns wide and about about 100 microns long, overlaps a portion of the first electrode with about 90 microns of its length extending onto the surface of the highly polished alumina substrate 12 beyond the region which will subsequently be covered by the cap. This band of non-porous electrically conductive material is electrically connected to the engine internal combustion control system. A non-porous material is required so that oxygen gas from the internal reference gas chamber cannot leak through the first porous platinum electrode.

The pump cell 16 comprises the conventional solid electrolyte material, preferably zirconia, partially or fully stabilized in its cubic form by the inclusion of about 4-8 mole percent yttria, a first electrode 28 overlaying the solid zirconia electrolyte film, and a second electrode 24 beneath the solid zirconia electrolyte film 26. The yttria stabilized zirconia film 26 is deposited to a thickness of about 0.1 to about 1.0 micron. The first electrode 28 is comprised of a sputtered porous platinum film, about 0.1 to about 1.0 micron thick, overlaying the solid zirconia electrolyte film. The non-porous electrically conductive film 29, about 0.1 to about 1.0 micron thick, overlaps the porous platinum electrode film. It is preferred that the thicknesses of the yttria stabilized zirconia, solid electrolyte film, porous platinum electrode, and non-porous electrically conductive film not exceed about 0.3 micron. Again, this amount of material appears optimal in order to ensure sufficient coverage without sacrificing sensor response time.

The second electrode 24 of the pump cell 16 is a sputtered cerium dioxide film upon which the solid zirconia electrolyte 26 and porous platinum electrode 28 rest. This ceria electrode 24 is also an oxygen reservoir for the pump cell. Accordingly, the ceria electrode and reservoir 24 is non-porous and no exposure to an external source of oxygen is necessary, as in other analogous devices. Oxygen ions are electrochemically pumped out of the internal reference gas chamber 30 through the yttria stabilized zirconia electrolyte 26 and into the walls of the ceria electrode and oxygen reservoir 24. Ceria is the preferred material for the second electrode and oxygen reservoir because it is capable of electronic and ionic conduction and has good stability at high non-stoichiometries.

The ceria film 24 may vary in thickness from about 0.01 to about 1.0 micron. The maximum thickness of the ceria film 24 is limited only by the practicalities of fabricating this device. The minimum thickness of the ceria film 24 required for the successful operation of this oxygen sensing device is theoretically 4 Angstroms, for a preferred internal reference gas chamber height of about 1.0 micron, as measured between the top surface of the porous platinum electrode 28 comprised within the pump cell 16 and the bottom surface of the thick film cap 32. Approximately 60 percent or more of the volume of oxygen contained within the chamber 30 should be located above the top surface of the porous platinum electrode 28 comprised within the pump cell 16, within the approximately one micron high gap. Oxygen in its solid state, as in cerium dioxide, is 2500 times more dense than oxygen is in its gaseous state. Therefore, the oxygen gas contained within the approximately one micron high chamber 30 reacts with only about the top 4 Angstroms of the ceria electrode and reservoir 24. Therefore, by miniaturizing the chamber volume and subsequently minimizing the number of oxygen molecules to be pumped, as we have accomplished in this invention, it is possible to pump the oxygen ions into the top few atomic layers of the ceria electrode 24 instead of through an electrode as in conventional internal reference, solid electrolyte oxygen sensors.

It is known that ceria may be depleted of up to about 15 percent of its oxygen content before any degradation of the ceria film occurs. Therefore, to ensure adequate surface coverage and structural integrity during operation, the ceria electrode film 24 is preferably deposited to a thickness of about 0.01 to about 1.0 micron. As a practical matter, the most preferred thickness of the ceria electrode film is about 0.3 micron.

The internal reference gas chamber 30 is formed by the following preferred method. A similar method is disclosed in European Pat. No. 0 104 636 to Shiraishi. A carbon film is deposited in an appropriate pattern to a thickness of about 1.0 micron as measured from the top surface of the porous platinum electrode 28 contained within the pump cell 16. The carbon film forms the volume that eventually becomes the internal reference gas chamber 30. It therefore covers all of the working surface area of the oxygen sensor, about a 100 micron square, except the first electrode 20 of the sense cell 14 that will contact the external exhaust gases, and portions of the ceria electrode 24 and two non-porous electrically conductive films 23 and 29 required to extend beyond the reference gas chamber 30 for electrical connection. The carbon film pattern also extends onto a portion of the alumina substrate 12 that is beyond the substrate area covered by the capping layer, to provide a connecting channel 34 and orifice 38 for removal of the carbon film after the cap is formed. This connecting channel 34 is serpentine shaped and approximately 700 microns long when elongated. The channel 34 has about four 180 degree bends, so that the channel requires only about a 100 micron square area on the alumina substrate 12. The channel 34 is about 10 microns wide at the interface 36 between the internal reference gas chamber 30 and the channel. The width of the channel gradually becomes larger as the channel progresses toward the orifice 38, where it is about 20 microns wide.

A durable, thick film, non-porous ceramic, preferably alumina, is plasma or flame sprayed or otherwise deposited onto the carbon film covering the working surface of the oxygen sensor, to a height of about 50 to 100 microns. It is patterned as a patch having a width and length of about 100 microns, to provide a hermetically sealing capping layer 32. The thick film alumina is also concurrently deposited to a thickness of about 50 to 100 microns to form a patch 32a that completely covers and seals the top surface of the 100 micron square area on the alumina substrate 12 having the serpentine carbon film pattern which will form the serpentine, tortous connecting channel 34. The sensor is then heated in air to a temperature of at least about 600° C., by which the carbon film is volatized and removed via the orifice 38 provided on the alumina substrate 12. The connecting channel 34 between the internal reference gas chamber 30 and the orifice 38 is patterned in an elongated serpentine shape so that the leak rate due to the orifice is significantly lower than the oxygen pump rate and therefore insignificant to the total oxygen sensor operation.

The orifice 38 and connecting passage 34 do not affect the oxygen sensor measurements during operation adversely when the pumping cycle is less than one second. In fact, I believe that they provide a long term benefit to the sensor integrity. They provide an escape passage for any impurity gases which may accumulate in the internal reference gas chamber.

The galvanic sense cell 14 can continuously determine the oxygen concentration in the exhaust gas by continuously monitoring the oxygen concentration differential between the external exhaust gas and the internal reference oxygen pressure. The galvanic pump cell 16 generates internal reference oxygen pressure by applying an appropriate polarity electrical potential between its two electrodes 24 and 28. Oxygen is pumped from the walls of the ceria electrode and oxygen reservoir 24, through the zirconia electrolyte 26, through the overlaying platinum electrode 28, and into the chamber 30, until the oxygen pressure in the chamber equals the oxygen partial pressure in the exhaust. This is detected by a zero voltage output between the sense cell electrodes 20 and 22. The zero output voltage of the sense cell 14 causes control circuitry (not shown) to reverse polarity of the electrical potential on the pump cell electrodes 24 and 28. This empties the internal reference gas chamber 30. When a predetermined threshold voltage is reached across the sense cell electrodes 20 and 22, one cycle is completed. The control circuitry will again reverse polarity on the pump cell electrodes 24 and 28, causing the internal reference gas chamber 30 to refill.

In this method of operation, the oxygen sensor 10 is continuously cycled between the two extremes corresponding to chamber full and chamber empty. The amount of time required to complete one cycle is directly related to the number of oxygen ions pumped. This corresponds to the concentration of oxygen, i.e., the partial presssure of oxygen, in the gaseous mixture being measured. The principle equation which describes this oxygen sensor operation is:

$$t = P(O_2)_{exh} \times V/IT \times C \times [e^{-E_{uf}/AT} - e^{-E_{if}/AT}]$$

where t is the period of oscillation, P is the partial pressure of oxygen in the exhaust, I is the absolute magnitude of the current pump, T is the absolute temperature of the cell, V is the internal reference chamber volume, and C is a collection of fixed geometry terms and fundamental constants, such as the number of electrons required to transport one oxygen ion.

My invention discloses a high precision, rapid response, electrochemical type oxygen sensor suitable for determining oxygen concentrations in lean automobile exhaust gases in which, after equilibration, the oxygen partial pressure can vary from almost zero up to about 0.08 atms. This sensor is well adapted to operate at temperatures varying between about 300° C. and 800° C. The response time of this sensor should be less than about 0.05 seconds. It should, therefore, be capable of providing an output signal indicative of a given oxygen partial pressure in a sensed gas within about 0.05 seconds of exposure to that sensed gas. Each change in that oxygen partial pressure would then result in a change in output signal about 0.05 seconds later.

The embodiments of the invention in which an exclusive property or privilege is claimed are defined as follows:

1. In a thin film, internal reference, solid electrolyte oxygen sensor having laterally disposed galvanic sense and internal reference oxygen pump cells on a non-ionically and non-electrically conductive substrate in which
   the galvanic sense cell comprises an yttria stabilized zirconia solid electrolyte layer on the substrate with two overlaying thin film porous electrodes on its surface that are laterally disposed with respect to one another, so that the first electrode may contact an external measuring gas and the second electrode may contact an internal reference gas;
   the galvanic internal reference oxygen pump cell comprises an yttria stabilized zirconia solid electrolyte layer laterally, non-contiguously disposed on the substrate with respect to the sense cell electrolyte layer, with an overlaying porous electrode, so that the porous electrode may also contact the internal reference gas; and
   hermetically bonded to the substrate over the porous electrode of the pump cell and the second porous electrode of the sense cell, and a gas impermeable cap providing a chamber for the internal reference gas, by which the porous electrode of both the galvanic pump and sense cells is exposed to an identical predetermined internal reference oxygen pressure;
   the improvement wherein said porous electrode in the galvanic pump cell has a thickness of about 0.1 micron to about 1.0 micron, said yttria stabilized zirconia electrolyte layer has a thickness of about 0.1 micron to about 1.0 micron, and a second electrode that is a thin film of ceria with a thickness of about 0.01 micron to about 1.0 micron dispersed on the opposite side of said electrolyte layer with respect to said porous electrode, said ceria film layer which functions as an internal oxygen reservoir for said pump cell; and
   the internal reference chamber volume is less than about 9000 microns$^3$, but greater than about 2500 microns$^3$, and the maximum height of the cavity as determined between the top surface of the platinum electrode contained within the galvanic pump cell and the bottom surface of the impermeable cap being less than about 1.0 micron;
   effective to provide a miniature, rapid response, highly precise oxygen partial pressure detector suitable for detecting air/fuel ratios for internal combustion engines operating with lean air/fuel mixtures.

2. An oxygen sensor of claim 1 wherein the galvanic sense and pump cells have an yttria stabilized zirconia solid electrolyte layer, about 0.1 to about 1.0 micron thick, and the porous electrodes of these cells are platinum, and the platinum ranges in thickness from about 0.1 to about 1.0 micron.

3. An oxygen sensor of claim 2 wherein the surface area of the platinum electrode for the galvanic pump cell comprises at least 50 percent of the substrate surface area enclosed by the reference chamber cap.

4. An oxygen sensor of claim 1 wherein the impermeable, hermetically sealed cap comprises a plasma or flame sprayed durable, thick film ceramic.

* * * * *